United States Patent [19]

Striegler

[11] 4,174,629
[45] Nov. 20, 1979

[54] DETECTION OF DRILLING OIL FILTRATE INVASION IN A CORE

[75] Inventor: John H. Striegler, Richardson, Tex.

[73] Assignee: Atlantic Richfield Company, Los Angeles, Calif.

[21] Appl. No.: 954,391

[22] Filed: Oct. 25, 1978

[51] Int. Cl.$^2$ .............................................. E21B 49/02
[52] U.S. Cl. ...................... 73/153; 73/61.4; 175/40
[58] Field of Search ..................... 73/153, 61.1 C, 155, 73/61.4, 151, 53; 166/250; 175/40, 46, 50

[56] References Cited

U.S. PATENT DOCUMENTS

| 2,790,016 | 4/1957 | Lanneau | 73/61.1 C X |
| 3,990,298 | 11/1976 | Deans | 73/155 |

Primary Examiner—Jerry W. Myracle
Attorney, Agent, or Firm—M. David Folzenlogen

[57] ABSTRACT

During the analysis of sample oil from an oil bearing formation, drilling fluid oil filtrate invasion into a cored oil bearing subsurface formation is detected in a way that does not require the use of special chemicals or tracers. Significant oil filtrate invasion is detected by determining the relative quantities of the same two hydrocarbon materials in the formation oil, drilling oil, and sample oil. Preferably, each hydrocarbon material is one or more hydrocarbons selected from the group consisting of hydrocarbons with eight carbon atoms through hydrocarbons with thirty-five carbon atoms. The drilling oil may be topped crude oil or formation oil that has had most of the hydrocarbons with one carbon atom through six carbon atoms removed. Fuel oil may have been added to the topped oil.

15 Claims, 1 Drawing Figure

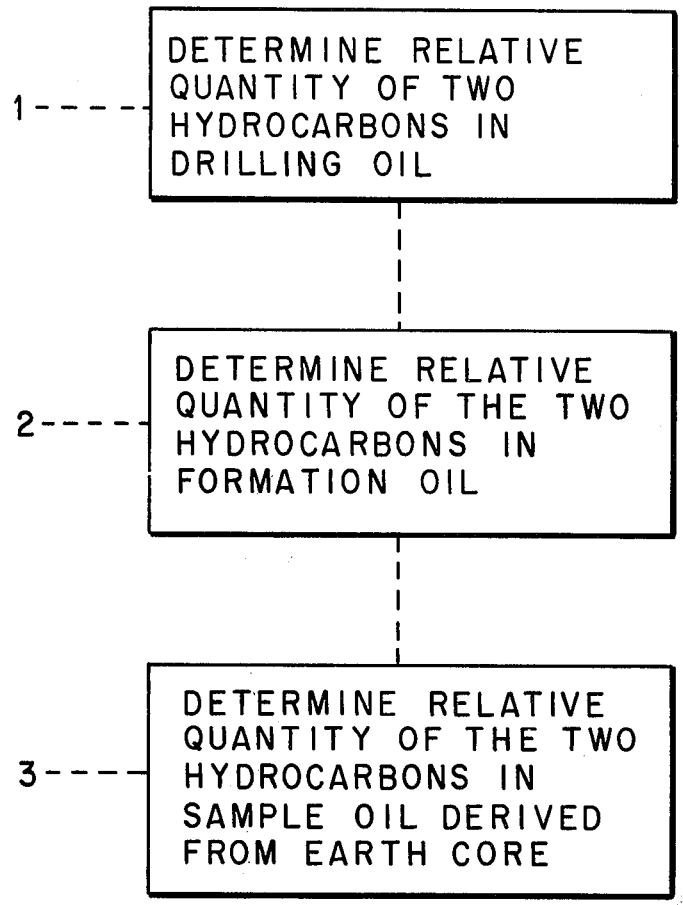

DETECTION OF DRILLING OIL FILTRATE INVASION IN A CORE

BACKGROUND OF THE INVENTION

This invention pertains to the analysis of an oil bearing core that has been subjected to an oil base drilling fluid.

An oil productive subsurface formation typically contains varying amounts of oil, gas and water in a porous matrix. Sometimes, it is important to determine the amount of oil present in order that various oil recovery techniques may be evaluated. For this and other purposes, cores are frequently taken to determine the amount of oil in the formation. The fluids are removed from the core and this pulse several measurements enables the oil saturation to be determined.

Sometimes it is desirable to use an oil base drilling fluid. For example, oil base drilling fluids have advantages in an unstable formation, or at higher temperatures, or when hydrogen sulfide is present. The typical oil base drilling fluid is comprised of an oil and chemicals and solids designed to control formation pressures, suspend drill cuttings and reduce fluid loss to the formation. The drilling fluid is usually at a higher pressure, for example, a couple of hundred pounds per square inch, than the formations which are subjected to the drilling fluid. Under certain conditions, the oil in the oil base drilling fluid invades the formation changing the oil concentration of the formation in the vicinity of the bore hole. When oil leaks in this fashion into the formation, the solids in the drilling fluid filter out on the face of the formation and the filter cake should stop further invasion of oil from the drilling fluid.

When a core is analyzed, it is important to know if the oil in the core has been significantly invaded by filtrate oil from the drilling fluid. It is standard practice to use a tracer chemical in a drilling fluid when it is important that drilling fluid invasion be determined. Tracer materials must be tested to determine their effects on drilling fluids and chemicals, their reaction with gases, their purity, their absorption characteristics on the filter cake or in the formation, solubility, and effects on drilling equipment and related facilities. Tracer materials are costly and frequently hazardous to drilling and core handling personnel. Moreover, the well that is being cored may be in a remote area. The drawbacks of tracer materials and the need for an improved system for detecting appreciable oil filtrate invasion has long existed.

In this invention, noticeable oil filtrate invasion is determined without the use of a separate tracer chemical. These and other advantages will be apparent from the following disclosure and appended claims.

SUMMARY OF THE INVENTION

Oil base drilling fluid invasion into a subsurface core taken from an oil-bearing formation is detected without the use of tracers by comparative analysis of the same hydrocarbon materials in the drilling oil, formation oil and core oil. The relative quantities of at least two different hydrocarbon materials must be determined for each of the three oils. The oils may be derived from producin the formation, filtering the drilling fluid, and extracting oil from the core. The oil used in the drilling fluid must have a different hydrocarbon analysis from the formation oil and may be crude oil or produced formation oil that has been topped for removal of most of the hydrocarbons with six carbon atoms and less. Fuel oil may be added to obtain the desired drilling fluid properties. Preferably, each hydrocarbon material is one or more hydrocarbons selected from the group consisting of hydrocarbons with eight to thirty-five carbon atoms. The hydrocarbon materials may be based on boiling point. The relative quantities of the hydrocarbon materials may be determined using the principles of chromatography or mass spectorphotometry.

BRIEF DESCRIPTION OF THE DRAWING

The drawing shows the three essential steps for detecting oil filtrate invasion.

DETAILED DESCRIPTION OF PREFERRED EMBODIMENT

This disclosure relates to the analysis of cores taken from an oil-bearing subsurface formation when the formation has been subjected to the presence of an oil base drilling fluid or workover fluid. The analytical method is generally applicable to formations that had not produced oil prior to coring or that had been previously produced. The method is primarily directed to detecting noticeable oil base drilling fluid invasion into the formation.

Coring is the most commonly used technique for acquiring information about the amount of fluids in a subterranean oil-bearing formation lying below the surface of the earth. Cores are usually aken with a core barrel while drilling, but small cores may also be taken with a sidewall coring device. When the core is brought to the surface and analyzed for fluid content, it is important to know whether the core data is reliabe, expecially as to oil saturation or content. Sometimes, the formation is subjected to the elevated pressure of an oil base drilling or workover fluid. These fluids typically contain an oil and fluid loss control additives. The oil-bearing formation is porous. If fluid loss additives in the drilling fluid do not prevent it, oil from the drilling fluid seeps into the formation. This oil invasion can effect the oil saturation especially when the formation adjacent the borehole contains mobile water or gas. The analytical method of this disclosure is concerned with detecting noticeable or predetermined amounts of drilling oil invasion into a core taken from the oil-bearing formation without the use of special tracer chemicals.

The analytical method depends on determining the relative quantities of two different hydrocarbon materials in the formation oil, drilling oil, and a sample oil derived from a core taken from the formation after the formation has been subjected to the presence of an oil base drilling fluid. The relative quantities of the same two hydrocarbon materials are determined in each oil. For purposes of this disclosure, the words "hydrocarbon materials" include a single hydrocarbon or a combination or range of hydrocarbons. The hydrocarbon materials may be based on a boiling point range, for example, the type of boiling points used in liquid chromatography. The words "relative quantity" refer to any measurement that provides a value that indicates the percentage of hydrocarbon material in the whole oil. For example, in chromatography, this may be a value representative of an area under a curve printed on a chromatographic chart which has been eluted between the next lower alkane and the next higher one and the total area under the curve, or a value representative of the number of chromatographic counts for the selected hydrocarbon material and for the total number of counts in the sample. The hydrocarbon determinations for each oil do not need to be taken in any sequence, but it is preferred that the determinations be taken on the same day as this reduces the chances for analytical errors. For increased sensitivity and reliability, the relative quantities of more than two hydrocarbon materials may be determined. For example, chromatographic information across the entire range of hydrocarbons may be compared or the chromatographic data may be fed to a computer which will compare increments of the hydrocarbon measurements and determine the degree of change.

The relative quantities of the two or more hydrocarbons determined in the drilling oil and formation oil must be measurably different, that is, the quantities must be sufficiently different that the change in hydrocarbon analysis caused by invasion of ten percent by weight of drilling oil into formation oil will be within the repeatability or accuracy of the particular analytical method being used, for example, chromatography or mass spectrophotometry. For best results, it is preferred that each hydrocarbon material is one or more hydrocarbons selected from the group consisting of hydrocarbons with eight to thirty-five carbon atoms. This range of hydrocarbons is workable while not being unduly volatile. Properly performed, chromatographic measurements for the type of hydrocarbons found in crude oils and for hydrocarbons with eight carbon atoms or more per molecule may be repeated to an accuracy of one percent, for example, for a ten percent by weight value, the accuracy would be 9.9 to 10.10 percent. The hydrocarbon materials or range of carbon atoms can be selected to provide sufficient difference between the hydrocarbon analysis of the drilling oil and the formation oil.

The analytical method of this disclosure is comprised of determining the relative quantities of two or more different hydrocarbon materials in the drilling oil. This is step 1 of the drawing. The relative quantities of the same two hydrocarbon materials is also determined in the formation oil. This is step 2 of the drawing. As previously stated, the relative quantities of these hydrocarbon materials in the formation oil and the drilling oil are different by an amount such that the relative quantities of the hydrocarbons in a ten percent by weight drilling oil - ninety percent by weight formation oil mixture are measurably different from the relative quantities of the hydrocarbons in the drilling oil and formation oil. The relative quantities of the same hydrocarbon materials are also determined in a sample oil taken from the core to establish whether the core has been noticeably invaded by drilling oil when the core was subjected to the presence of oil base drilling fluid. This is step 3 of the drawing.

The formation oil is derived from producing oil from the formation either before or after coring. The sample oil is derived from the core. The sample oil may be obtained by standard means, for example, by centrifuging the core, or by solvent extraction or fluid displacement of the core. Solvent extraction is preferred.

As previously stated, the drilling oil used in the oil base drilling fluid must have two hydrocarbon materials that have relative quantities in the drilling oil different from the relative quantities of the same two hydrocarbon materials in the formation oil. If the formation oil analysis is unknown at the time of selection of the drilling oil, the drilling oil may be formulated in a way that does not naturally occur in crude oils. For example, the use or addition of fuel oil or the topping or distillation of crude oil to remove most of the hydrocarbons with one to six carbon atoms, and perhaps other hydrocarbon costs that are present in crude oil. If oil has been produced from the formation, it is preferred that the drilling oil be formation oil taken from a stock tank and topped to remove most of the hydrocarbons with one to six carbon atoms. This topped formation oil may be used with or without the addition of fuel oil, for example, kerosene or diesel oil. Since the analytical method is concerned with invasion of drilling oil from the oil base drilling mud into the formation, the drilling oil used in the analytical method may be derived from filtering the oil base drilling fluid to remove fluid loss additives or weighting solids. This assures that the drilling oil analysis accurately represents the analysis of drilling oil that might seep into the formation.

Table 1 shows a chromatographic hydrocarbon and temperature distribution analysis of a formation crude oil. Table 2 shows the same analysis for a drilling oil made up of a crude oil that has been topped and mixed with a fuel oil. The percentages are given in weight percent. The temperature is given in degrees Fahrenheit.

TABLE 1
FORMATION OIL ANALYSIS

| Hydrocarbon | | | | Distribution | | | |
|---|---|---|---|---|---|---|---|
| Hc | P.C. | Hc | P.C. | Temp. | P.C. | Temp. | P.C. |
| | | | | | | 650 | 38.76 |
| C4 | 0.00 | C20 | 2.78 | 100 | 0.92 | 700 | 44.71 |
| C5 | 1.01 | C21 | 2.62 | 150 | 1.09 | 750 | 50.39 |
| C6 | 0.54 | C22 | 2.48 | 200 | 1.99 | 800 | 55.54 |
| C7 | 1.83 | C23 | 2.32 | 250 | 4.21 | 850 | 60.68 |
| C8 | 2.90 | C24 | 2.18 | 300 | 7.61 | 900 | 65.63 |
| C9 | 3.14 | C25 | 2.03 | 350 | 11.35 | 950 | 69.51 |
| C10 | 3.08 | C26 | 1.88 | 400 | 15.32 | 1000 | 73.31 |
| C11 | 3.00 | C27 | 1.79 | 450 | 19.28 | 1050 | 76.74 |
| C12 | 2.84 | C28 | 1.73 | 500 | 24.74 | 1100 | 79.60 |
| C13 | 3.13 | C29 | 1.69 | 550 | 28.81 | | |
| C14 | 3.59 | C30 | 1.61 | 600 | 32.78 | | |
| C15 | 2.94 | C31 | 1.53 | | | | |
| C16 | 1.36 | C32 | 1.43 | | | | |
| C17 | 2.22 | C33 | 1.43 | | | | |
| C18 | 2.95 | C34 | 1.23 | | | | |
| C19 | 2.99 | C35 | 1.03 | | | | |

TABLE 2
DRILLING OIL ANALYSIS

| Hydrocarbon | | | | Distribution | | | |
|---|---|---|---|---|---|---|---|
| Hc | P.C. | Hc | P.C. | Temp. | P.C. | Temp. | P.C. |
| C4 | 0.00 | C20 | 2.49 | 100 | 0.00 | 650 | 52.95 |
| C5 | 0.00 | C21 | 1.99 | 150 | 0.00 | 700 | 57.60 |
| C6 | 0.00 | C22 | 1.76 | 200 | 0.00 | 750 | 61.57 |
| C7 | 0.02 | C23 | 1.63 | 250 | 0.04 | 800 | 65.25 |
| C8 | 0.48 | C24 | 1.54 | 300 | 1.26 | 850 | 68.92 |
| C9 | 3.12 | C25 | 1.43 | 350 | 7.04 | 900 | 72.42 |
| C10 | 5.54 | C26 | 1.34 | 400 | 14.91 | 950 | 75.15 |
| C11 | 6.03 | C27 | 1.28 | 450 | 22.69 | 1000 | 77.90 |
| C12 | 5.72 | C28 | 1.25 | 500 | 33.03 | 1050 | 80.44 |
| C13 | 5.93 | C29 | 1.20 | 550 | 39.91 | 1100 | 82.71 |
| C14 | 6.68 | C30 | 1.15 | 600 | 46.02 | | |
| C15 | 5.18 | C31 | 1.08 | | | | |
| C16 | 2.12 | C32 | 1.01 | | | | |
| C17 | 3.52 | C33 | 1.00 | | | | |
| C18 | 4.05 | C34 | 0.86 | | | | |
| C19 | 3.45 | C35 | 0.72 | | | | |

For purposes of this analytical method, hydrocarbon analysis of the formation oil in Table 1 is sufficiently different from the hydrocarbon analysis of the drilling oil. For example, a ten percent by weight mixture of drilling oil in formation would have a $C_{10}$–$C_{15}$ hydrocarbon analysis of 20.23 with a possible range 20.028 to 20.428. The $C_{20}$–$C_{25}$ hydrocarbon analysis would be 14.05 with a possible range of 13.909 to 14.191. The corresponding hydrocarbons in the drilling oil are 35.08 and 10.84. In the formation oil, the $C_{10}$–$C_{15}$ is 18.58 with a possible range of 18.394 to 18.766, and the $C_{20}$–$C_{25}$ analysis is 14.41 with a possible range of 14.265 to 14.554. The ratio of $C_{10}$–$C_{15}$ to $C_{20}$–$C_{25}$ hydrocarbons in the formation oil has a value of 1.289 with a possible range of 1.264 to 1.315. The ratio of $C_{10}$–$C_{15}$ to $C_{20}$–$C_{25}$ hydrocarbons in the sample oil has a value of 1.439 with a possible range of 1.411 to 1.469. Since the lowest ratio for the sample oil is 1.411 and the highest ratio for the formation oil is 1.311, the formation oil must have been invaded by drilling oil. The two hydrocarbon analyses provide means for checking the validity of the conclusion and for determining the amount of invasion.

The principle of the invention, a detailed description of one specific application of the principle, and the best mode in which it is contemplated to apply that principle have been described. It is to be understood that the foregoing is illustrative only and that other means and techniques can be employed without departing from the true scope of the invention defined in the following claims.

The embodiments of the invention in which an exclusive property or privilege is claimed are defined as follows:

1. In the analysis of sample oil derived from a core taken from a subsurface formation containing formation oil, said core having been subjected to the presence of an oil base drilling fluid using a drilling oil that has a hydrocarbon analysis different from said formation oil, the method comprising:
    a. determining the relative quantities of at least two different hydrocabon materials in said drilling oil;
    b. determining the relative quantities of said hydrocarbon materials in said formation oil, said relative quantities of said hydrocarbon materials in said formation oil being different from said relative quantities of said hydrocarbon materials in said drilling oil by an amount such that the relative quantities of said hydrocarbons in a mixture of said drilling oil and said formation oil containing ten percent by weight of said drilling oil are measurably different from the relative quantities of said hydrocarbons in said drilling oil and formation oil; and
    c. determining in said sample oil the relative quantities of said hydrocarbon materials to establish whether said core has been noticeably invaded by drilling oil when said core was subjected to the presence of said oil base drilling fluid.

2. The method of claim 1 wherein each of said hydrocarbon materials is selected from the group consisting of hydrocarbons with eight carbon atoms through hydrocarbons with thirty-five carbon atoms, or mixtures thereof.

3. The method of claim 1 wherein in step (a) said drilling oil is derived from filtering said oil has base drilling fluid and in step (b) said formation oil is derived from producing oil from said subsurface formation, and in step (c) said sample oil is derived from said core.

4. The method of claim 1 wherein the oil used in said oil base drilling fluid is comprised of topped crude oil that has had most of the hydrocarbons with one carbon atom through six carbon atoms removed.

5. The method of claim 4 wherein fuel oil has been added to said topped crude oil.

6. The method of claim 4 wherein the topped crude oil is topped formation oil that has had most of the hydrocarbons with one carbon atom through six carbon atoms removed.

7. The method of claim 6 wherein fuel oil has been added to said topped formation oil.

8. The method of claim 4 wherein each of said hydrocarbon materials is selected from the group consisting of hydrocarbons with eight carbon atoms through hydrocarbons with thirty-five carbon atoms, or mixtures thereof.

9. The method of claim 8 wherein fuel oil has been added to said topped crude oil.

10. The method of claim 8 wherein the topped crude oil is topped formation oil that has had most of the hydrocarbons with one carbon atom through six carbon atoms removed.

11. The method of claim 10 wherein fuel oil has been added to said topped formation oil.

12. The method of claim 4 wherein in step (a) said drilling oil is derived from filtering said oil base drilling fluid, and in step (b) said formation oil is derived from producing oil from said subsurface formation, and in step (c) said sample oil is derived from said core.

13. The method of claim 12 wherein fuel oil has been added to said topped crude oil.

14. The method of claim 12 wherein said topped crude oil is topped formation oil that has most of the hydrocarbons with one carbon atom through six carbon atoms removed.

15. The method of claim 14 wherein fuel oil has been added to said topped formation oil.

* * * * *